United States Patent
Kasuga et al.

[11] Patent Number: 6,027,775
[45] Date of Patent: Feb. 22, 2000

[54] CRYSTALLINE TITANIA AND PROCESS FOR PRODUCING THE SAME

[75] Inventors: Tomoko Kasuga, Aichi-ken; Masayoshi Hiramatsu, Nagoya, both of Japan

[73] Assignee: Chubu Electric Power Co., Inc., Nagoya, Japan

[21] Appl. No.: 08/937,885

[22] Filed: Sep. 25, 1997

[30] Foreign Application Priority Data

Sep. 30, 1996 [JP] Japan .................................. 8-259182

[51] Int. Cl.$^7$ .................................................. B29D 22/00
[52] U.S. Cl. ........................ 428/34.1; 428/34.4; 428/34.5
[58] Field of Search ................................ 428/34.1, 34.4, 428/34.5

[56] References Cited

FOREIGN PATENT DOCUMENTS 8-257399  10/1996  Japan .
9-70532   3/1997   Japan .

OTHER PUBLICATIONS

Journal of Materials Research, "Preparation of $TiO_2$–based Powders with High Photocatalytic Activities", Kasuga et al, vol. 12, No. 3, Mar., 1997, pp. 607–609.

Advanced Materials, "Semiconductor Nanotube Formation by a Two–Step Template Process", Hoyer, pp. 857–859 Adv. Mater, 1996, 8, N. 10 No Month.

Langmuir, "Formation of a Titanium Dioxide Nanotube Array", Hoyer, pp. 1411–1413 No Month.

Preprints of Annual Meeting of The Ceramic Society of Japan 1995 No Month, Apr. 1–3, 1995, p. 363, "Photocatalytic Property of $TiO_2$–$SiO_2$ Powders Prepared by a Sol–Gel Method", Kasuga et al Japan only.

Preprints of the 8th Autumn Symposium of The Ceramic Society of Japan 1996, Oct. 3–5, 1995, p. 167, "Photocatalytic of $TiO_2$–$SiO_2$ Powders Leached with Aqueous NaOH", Kasuga et al Japanese onlyl.

Preprints of Annual Meeting of The Ceramic Society of Japan 1996, Apr. 2–4, 1996, pp. 170, "Improvement of Photocatalytic Activity of $TiO_2$–based Powders Prepared by a Sol–Gel Method", Kasuga et al Japanese only.

Preprints of the 76th Catalyst Discussion Society (A), Oct. 7–8, 1995, Held by Catalyst Academy and The Chemical Society of Japan, pp. 24–25 Japanese only.

Preprints of the 78th Catalyst Discussion Society (A), Oct. 9–11, 1996, held by Catalyst Academy and The Chemical Society of Japan, p. 67 Japanese Language copy only.

Preprints of Symposium of Catalyst Chemistry Related to Light, Jun. 6, 1996, held by Rikagaku Kenkyusyo and Catalyst Academy, pp. 24–25 Japanese Language copy only.

*Primary Examiner*—Charles Nold
*Attorney, Agent, or Firm*—Nikaido, Marmelstein, Murray & Oram LLP

[57] ABSTRACT

Crystalline titania of which the crystal shape is a novel nanotube. This crystalline titania is produced by treating crystalline titania with an alkali. This crystalline titania is used as an ultraviolet absorber, a masking agent, an adsorbent and an optically active catalyst.

5 Claims, 2 Drawing Sheets

CRYSTALLINE TITANIA AND PROCESS FOR PRODUCING THE SAME

BACKGROUND OF THE INVENTION

1. Field of the Invention

Titania ($TiO_2$) is excellent in properties such as ultraviolet absorbability, adsorbability and the like. Accordingly, it has been widely used as a material in such applications as ① an ultraviolet absorber, a masking agent in an anti-sunburn agent, a paint, a film and the like; ② an absorber, an adsorbent, a deodorizer and the like.

Further, nowadays the superior photocatalytic activity of titania is given attention. The titania is applied to environmental cleanup or the like upon decomposition of carbonaceous gas or nitrogen oxides while utilizing the superior properties thereof, such as oxidation or reduction.

The improvement of the properties of titania, especially the photocatalytic activity in the above-mentioned usages has been in demand.

2. Description of Related Art

As one of the conventional technologies for improving the properties of titania, it is known that if titania is doped with $SiO_2$, the specific surface area can be increased.

In order to improve the photocatalytic activity, the present inventors tried to chemically treat the $TiO_2$ powder obtained by a sol-gel method, having large specific surface area, with an NaOH aqueous solution to improve the photocatalytic activity, and reported this technology in the following literature.

(1) "Preprints of Symposium of Catalyst Chemistry related to Light", Jun. 6, 1996, held by Rikagaku Kenkyusyo and Catalyst Academy, p. 24–25

(2) "Preprints of Annual Meeting of The Ceramic Society of Japan 1996", Apr. 2 to 4, 1996, p. 170

SUMMARY OF THE INVENTION

Taking aim at improving the catalytic activity as the properties of crystalline titania, further investigations were made. Meanwhile, it has been found that where the crystalline titania is treated with an alkali, if certain conditions are met, a titania crystal in a nanotube form, which has hitherto been unknown, is formed, leading to the accomplishment of the present invention.

It has been hitherto considered that the crystal shape of crystalline titania has only a spherical shape or a needle shape, whether it is an anatase type or a rutile type, so long as the present inventors know.

The present invention is to provide crystalline titania of a nanotube which has a novel crystal shape. The diameter of the nanotube varies depending on the production conditions and the like. It is approximately between 5 and 80 nm in many cases. The crystal structure which is easy to obtain is an anatase type.

This nanotube is formed by treating crystalline titania with an alkali. In order to increase the yield, the alkali treatment can be conducted at a temperature of from 18 to 160° C. using from 13 to 65 percent by outer weight of sodium hydroxide.

Since the nanotube is a hollow crystal, the specific surface area is increased as compared with a solid crystal such as a needle crystal, and the specific surface area in the volume occupied is more increased. Accordingly, it is expected to markedly improve the properties of the crystalline titania. Further, this crystal is expected to find novel use in filters and the like upon utilizing the nanotube shape.

DESCRIPTION OF THE PREFERRED EMBODIMENTS

Figure 1:
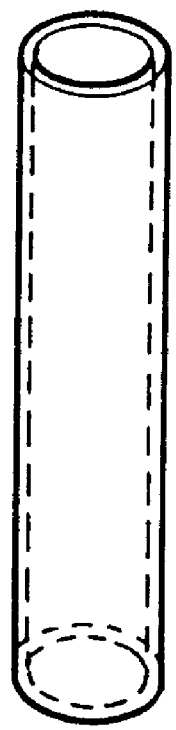
FIG. 1 is a view showing a model shape of crystalline titania in the present invention.
Figure 2:
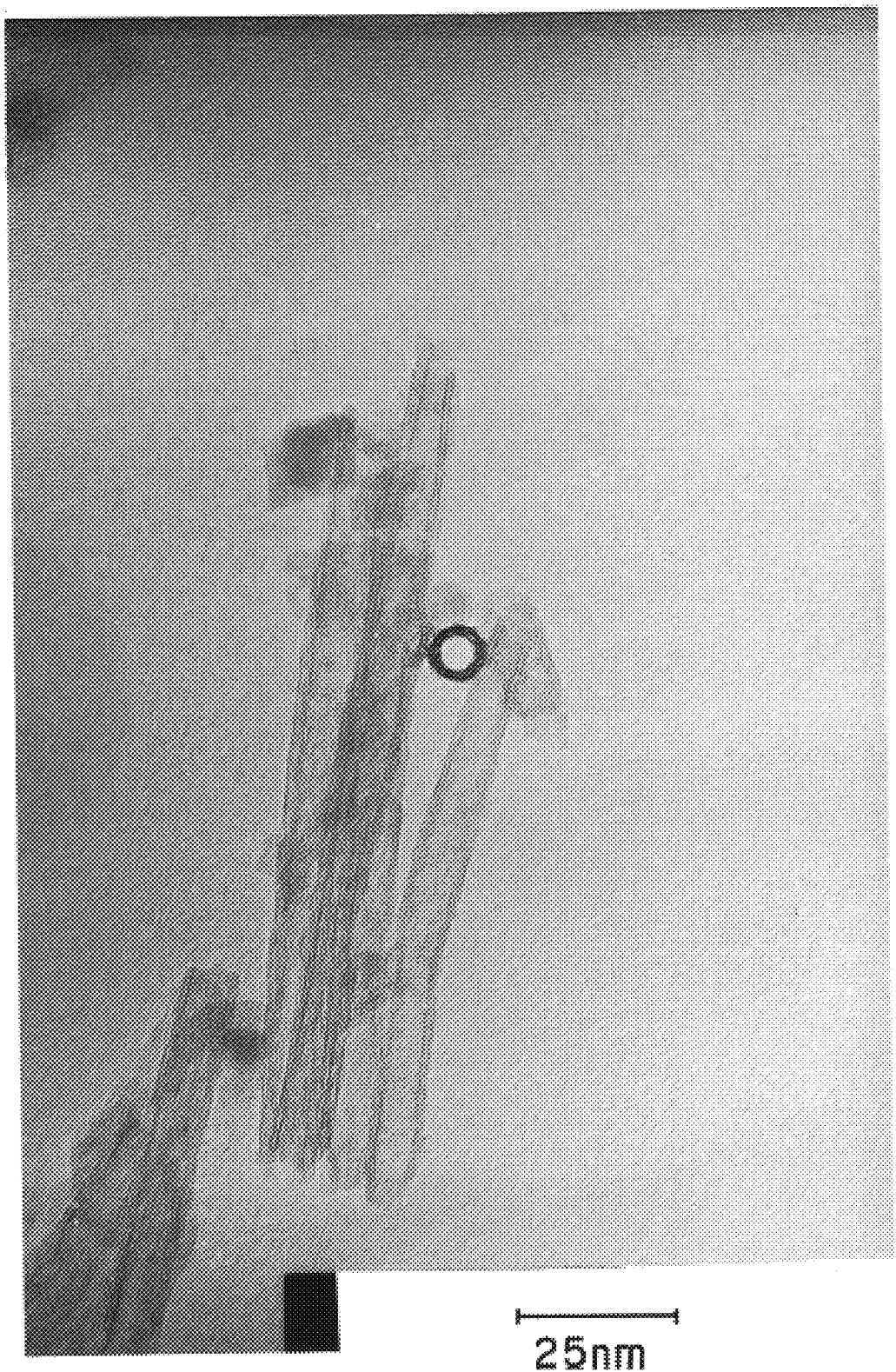
FIG. 2 is a transmission electron micrograph of Sample No. 1–11 (40%×110° C.×20 hrs) in Example.

The crystalline titania of the present invention is a nanotube as shown in FIG. 1.

The diameter of this nanotube varies depending on the production conditions. It is usually between approximately 5 and 80 nm. The length thereof also varies depending on the production conditions. It is usually between 50 and 150 nm. The thickness thereof is usually between 2 and 10 nm.

With respect to the crystal system of this nanotube, the anatase type is easily obtainable as shown in Tables 1 and 2.

The process for producing crystalline titania in the present invention is described below. In the following description, "% by weight" which refers to the alkali concentration means outer percent by weight.

The crystalline titania which has a nanotube shape in the present invention is produced by treating a titania powder with an alkali.

(1) Production of a titania powder

The titania powder (crystalline titania) used herein has a particle diameter of, usually from 2 to 100 nm, preferably from 2 to 30 nm whether it is an anatase type or a rutile type.

Examples thereof include titania powders produced from a titanium ore such as anatase, rutile, brookite and the like by the following known liquid phase method, vapor deposition method or sol-gel method.

"Vapor deposition method" here referred to is a method in which titania is produced by hydrolyzing a titanium ore with a heating strong acid such as sulfuric acid or the like, and heating the resulting hydrous titanium oxide at from 800 to 850° C.

"Liquid phase method" here referred to is a method in which titania is produced by contacting $TiCl_4$ with $O_2$ and $H_2$.

"Sol-gel method" here referred to is a method in which titania is produced by hydrolyzing titanium alkoxide including $Ti(OR)_4$ in an alcohol aqueous solution to form a sol, adding a hydrolase to the sol, allowing the mixture to stand for gelation, and heating the gel.

(2) Alkali treatment

In the alkali treatment, a titania powder is dipped in from 13 to 65% by weight of sodium hydroxide at a temperature of from 18 to 160° C. for from 1 to 50 hours. Preferably, it is dipped in from 18 to 55% by weight of sodium hydroxide at a temperature of from 18 to 120° C. More preferably, it is dipped in from 30 to 50% by weight of sodium hydroxide at a temperature of from 50 to 120° C. for from 2 to 20 hours. At this time, when the alkali concentration is high, the temperature may be low (refer to Sample Nos. 1–9 and 2–4). When the temperature is high, the alkali concentration may be relatively low (refer to Sample Nos. 1–8 and 2–3).

When the concentration of sodium hydroxide is less than 13% by weight, the reaction time is too long to form a tube, and it is not efficient from the industrial viewpoint. When it exceeds 65% by weight, the tube is hardly formed (refer to Sample Nos. 1–15, 1–16, 1–17, 2–10, 2–11 and 2–12). When the temperature is less than 18° C., the reaction time for forming a tube is prolonged. When the temperature exceeds 160° C., the tube is hardly formed.

As supported in Examples to be described later, the nanotube crystal aggregate can hardly be produced without the above-mentioned ranges. At this time, the alkali treatment may be conducted in an open vessel, that is, under normal pressure (at atmospheric pressure). It is, however, advisable to conduct it in a sealed vessel. The evaporation of water is suppressed in the sealed vessel to stabilize the alkali concentration. When the temperature is increased to 100° C. or more in the sealed vessel, the pressure is increased, and a nanotube having a small diameter is easily produced as compared with the alkali treatment in an open vessel. When the alkali treatment is conducted in the sealed vessel under increased pressure of 1.5 atm (calculated), a nanotube having a small diameter of from 5 to 10 is obtained.

The alkali treatment includes a step of water-washing as a finalstep. It is advisable to neutralize the resulting product with an inorganic acid such as dilute hydrochloric acid or the like.

(3) Heat treatment

The above-obtained nanotube titania may further be heat-treated at from 200 to 1,200° C. for from 10 to 400 minutes, preferably at from 300 to 800° C. for from 60 to 160 minutes. This heat treatment is expected to improve the crystallinity of $TiO_2$ and to increase the catalytic activity. The nanotube does not collapse through this heat treatment. Further, it does not collapse either upon using a pulverizer.

(4) Use

The specific surface area of the above-obtained nanotube titania in the present invention is by far larger than that of the spherical or needle crystal.

Consequently, when this titania is used as an ultraviolet absorber, a masking agent, an adsorbent or an optically active catalyst, an increase in the specific surface area can be expected, and especially the specific surface area per unit volume can be greatly improved.

When this titania is used as a catalyst, it may be ordinarily supported on a metal such as platinum, nickel, silver or the like.

This nanotube titania can be used in such applications as ① a filter; ② a material with a new performance which is obtained by inserting an organic, inorganic, or metal material therein; and ③ a magnetic substance with new magnetic properties which is obtained by inserting a magnetic material therein.

EXAMPLES

The present invention is illustrated specifically by referring to the following Example.

(1) Production of starting crystalline titania

In order to give a composition of the formula

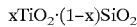

$xTiO_2 \cdot (1-x)SiO_2$ wherein x is 1 or 0.8, commercial tetraisobutoxytitanium and tetraethoxysilane were dissolved in an ethanol solution to conduct hydrolysis. To the resulting sol was added dilute hydrochloric acid as a hydrolase, and the mixture was allowed to stand for gelation.

The gel was heated with an electric oven at 600° C. for 2 hours. Then, the heated product was pulverized using an agate mortar to obtain a fine powder.

The following two types of starting crystal titania, 1) and 2), were prepared by this sol-gel method.

1) $TiO_2$ . . . average particle diameter: approximately 15 nm, specific surface area: 50 $m^2/g$ 2) $0.8TiO_2 \cdot 0.2SiO_2$ . . . average particle diameter: approximately 6 nm specific surface area: 10 $m^2/g$ Further, the following commercial crystal titania A was used a starting crystal.

3) Commercial crystal titania A

Anatase-type crystal titania ($TiO_2$) produced by reacting an ilmenite ore with sulfuric acid by a vapor deposition method.

average particle diameter: approximately 20 nm specific surface area: 50 $m^2/g$ (2) Conditions of alkali treatment Each of the titania powders was treated with alkali under conditions shown in Tables 1 and 2 (those other than Sample No. 1–12 and 2–7 were treated in a sealed vessel). The treated powders were subsequently neutralized with 0.1 N-HCl aqueous solution. In this manner, the test powders were prepared.

Each of the test powders was dispersed in an ethanol aqueous solution. A droplet of the dispersion was dropped on a test stand using a pipet, and observed using a transmission electron microscope to estimate the shape of the crystalline titania.

The results are shown in Tables 1 and 2. From the results in these tables, it is clear that no nanotube crystalline titania is obtained when the alkali concentration is too low or too high.

In Tables 1 and 2, each judgements is indicated as follows;

"x": A Comparative Example not within the present invention

"Δ": An Example which produces a nanotube partially

"○" and "⊚": An Example which produces a nanotube excellently

The judgements of "○" or "⊚" depend on a specific surface area of each sample. The judgements of them are not always proper when a product is required other properties.

In Tables 1 and 2, the terms have the following meanings.

"%": outer percent by weight

"tube/particle": Particles are incorporated in tubes

"particle/tube": Tubes are incorporated in particles.

In the crystalline titania in Table 1, x in the $SiO_2$ component was reduced to approximately 0.01 through the alkali treatment. As shown in Table 2, even when the starting crystalline titania was composed of 100% $TiO_2$, the nanotube titania crystal was obtained. It is thus clear that the precipitation of titania nanotube has nothing to do with the addition of $SiO_2$.

TABLE 1

Composition: 0.8 $TiO_2 \cdot 0.2\ SiO_2$

| Sample No. | Conditions of alkali treatment | Type and shape of crystal precipitated | | Specific surface area (m²/g) | Judgement |
|---|---|---|---|---|---|
| 1-1  | 2.5% × 100° C. × 60h       | anatase | particle      | 230 | x |
| 1-2  | 5.0% × 100° C. × 60h       | ↑ | ↑                   | 230 | x |
| 1-3  | 10% × 100° C. × 20h        | ↑ | ↑                   | 230 | x |
| 1-4  | 15% × 60° C. × 20h         | ↑ | tube/particle       | 250 | Δ |
| 1-5  | 15% × 150° C. × 5h         | ↑ | ↑                   | 250 | Δ |
| 1-6  | 20% × 20° C. × 20h         | ↑ | ↑                   | 250 | Δ |
| 1-7  | 20% × 60° C. × 20h         | ↑ | ↑                   | 250 | Δ |
| 1-8  | 20% × 110° C. × 20h        | ↑ | tube                | 300 | ○ |
| 1-9  | 40% × 20° C. × 20h         | ↑ | ↑                   | 320 | ○ |
| 1-10 | 40% × 60° C. × 20h         | ↑ | ↑                   | 340 | ⊙ |
| 1-11 | 40% × 110° C. × 20h        | ↑ | ↑                   | 420 | ⊙ |
| 1-12 | 40% × 110° C. × 10h (reflux) | ↑ | ↑                 | 480 | ⊙ |
| 1-13 | 60% × 60° C. × 20h         | ↑ | particle/tube       | 400 | Δ |
| 1-14 | 60% × 60° C. × 40h         | ↑ | ↑                   | 400 | Δ |
| 1-15 | 68% × 60° C. × 2h          | — | particle            | 320 | x |
| 1-16 | 68% × 60° C. × 30h         | — | ↑                   | 350 | x |
| 1-17 | 68% × 110° C. × 20h        | — | ↑                   | 400 | x | x: Comparative Example (no good)
Δ: Example (fair)
○: Example (good)
⊙: Example (excellent)

TABLE 2

Composition: TiO$_2$

| Sample No. | Conditions of alkali treatment | Type and shape of crystal precipitated | | Specific surface area (m$^2$/g) | Judgement |
|---|---|---|---|---|---|
| 2-1 | 20% × 20° C. × 20h | anatase | tube/particle | 200 | Δ |
| 2-2 | 20% × 60° C. × 20h | ↑ | ↑ | 200 | Δ |
| 2-3 | 20% × 110° C. × 20h | ↑ | tube | 300 | ○ |
| 2-4 | 40% × 20° C. × 20h | ↑ | ↑ | 200 | ○ |
| 2-5 | 40% × 60° C. × 2h | ↑ | ↑ | 400 | ⊙ |
| 2-6 | 40% × 110° C. × 20h | ↑ | ↑ | 420 | ⊙ |
| 2-7 | 40% × 110° C. × 20h (reflux) | ↑ | ↑ | 500 | ⊙ |
| 2-8 | 60% × 60° C. × 20h | ↑ | particle/tube | 400 | Δ |
| 2-9 | 60% × 60° C. × 40h | ↑ | ↑ | 400 | Δ |
| 2-10 | 68% × 60° C. × 10h | — | particle | 300 | x |
| 2-11 | 68% × 60° C. × 20h | — | ↑ | 350 | x |
| 2-12 | 68% × 110° C. × 20h | — | ↑ | 400 | x |
| 2-13 | 40% × 110° C. × 20h ✱ | anatase | tube | 300 | ○ |

✱: Commercial product A
x: Comparative Example (no good)
Δ: Example (fair)
○: Example (good)
⊙: Example (excellent)

What is claimed is:

1. A crystalline titania having a nanotube crystal shape with a diameter of between 5 and 80 nm.

2. The crystalline titania of claim 1, wherein the crystal structure is an anatase type.

3. A crystalline titania having a nanotube crystal shape and a wall thickness of 2 to 10 nm.

4. The crystalline titania of claim 3, wherein the crystal structure is an anatase type.

5. A crystalline titania having a nanotube crystal shape with a diameter of between 5 and 80 nm and a wall thickness of 2 to 10 nm.

* * * * *